United States Patent [19]

Malherbe

[11] 4,389,321
[45] Jun. 21, 1983

[54] 2,3-DIHYDROPERIMIDINES AS ANTIOXIDANTS FOR LUBRICANTS

[75] Inventor: Roger F. Malherbe, East Northport, N.Y.

[73] Assignee: Ciba-Geigy Corporation, Ardsley, N.Y.

[21] Appl. No.: 334,860

[22] Filed: Dec. 28, 1981

[51] Int. Cl.[3] .................. C10M 1/38; C10M 1/32; C10M 1/44
[52] U.S. Cl. .................. 252/47; 252/49.9; 252/50; 252/51.5 R; 252/400 A; 252/401; 252/402; 252/403
[58] Field of Search .............. 252/50, 51.5 R, 47, 252/49.9, 400 A, 401, 402, 403

[56] References Cited

U.S. PATENT DOCUMENTS

| | | | |
|---|---|---|---|
| 2,162,207 | 6/1939 | Moran et al. | 252/47 X |
| 2,223,411 | 12/1940 | Fuller et al. | 252/51.5 R X |
| 3,480,635 | 11/1969 | Altwicker | 252/50 X |
| 3,535,243 | 10/1970 | Chao et al. | 252/50 X |
| 3,634,248 | 1/1972 | Andress, Jr. | 252/50 X |

OTHER PUBLICATIONS

Liebigs Annalen, 365, 135 (1909).
Yamato et al., J.A.C.S., vol. 103, No. 14, p. 4186–4194 (1981).

Primary Examiner—Andrew Metz
Attorney, Agent, or Firm—Harry Falber

[57] ABSTRACT

Lubricants stabilized against oxidative degradation by the incorporation therein of 2,3-dihydroperimidine derivatives as well as certain 2,3-dihydroperimidines within the indicated group.

5 Claims, No Drawings

2,3-DIHYDROPERIMIDINES AS ANTIOXIDANTS FOR LUBRICANTS

This invention relates to lubricant compositions which are stabilized against oxidative decomposition by the addition of certain 2,3-dihydroperimidine derivatives. More particularly, these compounds are 2,3-dihydroperimidines substituted in the 2-position.

It is known to stabilize lubricants by the addition of antioxidants such, for example, as sterically hindered phenols, derivatives of p-phenylene diamine or of diphenylamine in order to avoid decomposition, sludge formation, viscosity increases, and the like. U.S. Pat. No. 3,535,243 also discloses the use of diaminonaphthalenes as antioxidative additives for ester lubricants. However, in mineral oils the solubility of these additives is too low for practical use.

It has now been found that certain derivatives of 2,3-dihydroperimidine show surprisingly high stabilizer activity and sufficient solubility in a wide variety of mineral and synthetic oils. Thus, the subject matter of the instant invention is a lubricant composition comprising a mineral oil, a synthetic oil or mixtures thereof and an antioxidative compound corresponding to formula I,

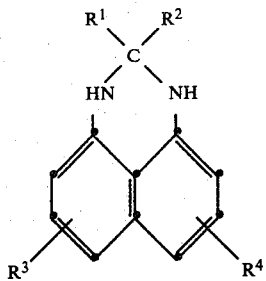

wherein $R^1$ is hydrogen or alkyl having 1 to 20 carbon atoms; $R^2$ is alkyl having 1 to 20 carbon atoms which may be unsubstituted or substituted by a phosphono group or interrupted by O or S, alkenyl having 3 to 16 carbon atoms, or aryl having 6 to 10 carbon atoms which may be unsubstituted or substituted by lower alkyl, hydroxyl, halogen or di(lower)alkylamino, or $R^1$ and $R^2$ together with the carbon atom to which they are attached are cycloalkane of 5 to 25 carbon atoms, alkylcycloalkane of 6 to 25 carbon atoms or cycloalkylcycloalkane of 9 to 25 carbon atoms; and $R^3$ and $R^4$ are independently hydrogen or alkyl having 1 to 12 carbon atoms or $R^3$ and $R^4$ together are 1,2-ethylene in the peri-position.

$R^1$ and $R^2$ as alkyl may be straight- or branched-chain and may be, e.g. methyl, ethyl, propyl, isopropyl, n-butyl, isobutyl, n-pentyl, isoamyl, n-hexyl, 2-ethylbutyl, n-octyl, 2-ethylhexyl, isononyl, n-decyl, isoundecyl, n-dodecyl, 2,4-dimethylpentyl, 2,4,6-trimethylheptyl, n-hexadecyl, n-octadecyl or n-eicosyl. $R^1$ and $R^2$ as alkyl are preferably branched-chain alkyl having 4 to 18 carbon atoms. $R^2$ may also be alkyl interrupted by O or S such, e.g, as 3-oxanonyl, 2-methyl-3-oxaheptyl, 3-thiaheptyl or 2-methyl-3-thia-pentadecyl. $R^2$ may further be alkyl substituted by a phosphono group, i.e. the group $-P(O)(OR^5)_2$ wherein $R^5$ is lower alkyl or phenyl. Examples of such an $R^2$ group are, e.g., 2-diethylphosphono-ethyl, 2-methyl-2-dimethylphosphono-propyl or 2-methyl-2-diphenylphosphono-propyl. $R^2$ as alkenyl includes, for example, 1-propenyl, 10-dodecenyl or 2-pentyl-1-nonadecenyl.

$R^2$ as aryl or substituted aryl may be, e.g. phenyl, 4-chlorophenyl, 4-tert.butylphenyl, 2-hydroxyphenyl, 4-dimethylaminophenyl, 1-naphthyl or 2-hydroxy-1-naphthyl.

If $R^1$ and $R^2$ together with the carbon atom to which they are attached form cycloalkane, alkyl- or cycloalkylcycloalkane groups, the cycloalkane group may be monocyclic or polycyclic. Examples of such cyclic groups are cyclopentane, cyclohexane, mono- or dimethylcyclohexane, 4-tert.butylcyclohexane, 4-dodecylcylohexane, 2-, 3- or 4-cyclohexyl cyclohexane, bicyclo[4.4.0]decane (decahydronaphthalene), tricyclo[5.2.1.0$^{2,6}$]decane, cyclooctane or cyclododecane.

$R^3$ and $R^4$ as alkyl may be, e.g. methyl, ethyl, isopropyl, tert.butyl, n-hexyl, isooctyl or n-dodecyl. These alkyl groups may be attached in the meta- or para-position to the nitrogen, i.e., in position 5, 6, 7 or 8 of the perimidine ring system.

When $R^3$ and $R^4$ are 1,2-ethylene, this group is attached in peri-position, i.e. in position 6 and 7 of the perimidine ring system.

Within the given definition of lubricant stabilizers, there are preferred classes. One preferred class includes compounds of formula I wherein $R^1$ is hydrogen or branched-chain alkyl having 4 to 18 carbon atoms and $R^2$ is branched-chain alkyl having 4 to 18 carbon atoms.

Another preferred class includes compounds of the formula I wherein $R^1$ and $R^2$ together with the carbon atom to which they are attached, form a cycloalkane, alkylcycloalkane or cycloalkylcycloalkane group having 10 to 20 carbon atoms.

A third preferred class includes compounds of formula I wherein $R^3$ and $R^4$ together form a 1,2-ethylene bridge in the peri-position.

Examples of compounds of formula I usable as antioxidative oil additives include the following compounds:
2,2-diethyl-2,3-dihydroperimidine
2-methyl-2-isobutyl-2,3-dihydroperimidine
2-methyl-2-dodecyl-2,3-dihydroperimidine
2,2-dinonyl-2,3-dihydroperimidine
2-undecyl-2,3-dihydroperimidine
2-methyl-2-phenyl-2,3-dihydroperimidine
2-methyl-2-naphthyl-2,3-dihydroperimidine
2-heptyl-2-phenyl-2,3-dihydroperimidine
2,3-dihydroperimidine-2-spirocyclohexane
2,3-dihydroperimidine-2-spirocyclododecane
2,3-dihydroperimidine-2-spiro(decahydro-1-naphthalene)
2,2-dinonyl-2,3-dihydroaceperimidine
2-methyl-2-isoamyl-2,3-dihydroaceperimidine
2-heptyl-2,3-dihydroaceperimidine
2-methyl-2-phenyl-2,3-dihydroaceperimidine
2,3-dihydroaceperimidine-2-spiro(4-t-amylcyclohexane)
2,3-dihydroaceperimidine-2-spirododecane
2-(o-hydroxyphenyl)-2,3-dihydroaceperimidine
2,2-(N-methyl-3′-aza-pentaethylene)-2,3-dihydroperimidine The lubricant may be an oil or a grease based on mineral or synthetic oils, these lubricants being well known to those skilled in the art. The term mineral oil includes all mineral oils used for lubricant purposes, such as hydrocarbon mineral oils. The synthetic oil may be, for instance, an aliphatic or aromatic carboxylic ester, a polymeric ester, a polyalkylene oxide, a phosphoric acid ester, polyalphaolefins, or a silicone. Greases may be obtainable from these by adding metal soaps or similar thickeners.

The amount of compound of formula I added to the lubricant depends on the sensitivity of the oil base to oxidation and on the desired degree of protection. Generally, 0.01 to 2% by weight will be added, and preferably 0.05 and 0.5%. The compounds of formula I may be used in combination with other antioxidants known as oil additives. Examples thereof are aromatic amines, hindered phenols, aliphatic or aromatic phosphites, esters of thiodipropionic or thiodiacetic acid or salts of dithiocarbamic or dithiophosphoric acids.

Such antioxidant combinations may show a synergistic action, i.e., the stabilizing effect of such a mixture being greater than the sum of the performances of the individual antioxidants. Such synergistic performance is obtained when combining compounds of formula I with aromatic amines or hindered phenols or with both types of antioxidants.

The lubricant composition may also contain other additives, such as metal-passivating agents, rust inhibitors, viscosity regulators, pour point depressants, dispersing agents or detergents, said additives being widely known and used in lubricants.

The perimidine compounds of formula I can be prepared by known methods of condensation of the corresponding 1,8-diaminonaphthalenes of formula II

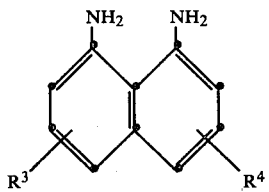
(II)

wherein $R^3$ and $R^4$ are as previously defined, with ketones or aldehydes of the formula

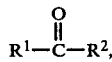

wherein $R^1$ and $R^2$ are as previously defined. The water formed in this reaction may be distilled off as an azeotropic mixture with toluene or xylene as is described in Liebigs Annalen 365, 135 (1909). The reaction may be catalyzed by acids, such as propionic acid, toluene sulfonic acid or trichloroacetic acid. Another method of preparing these compounds proceeds by reduction of the corresponding 1,8-dinitronaphthalenes in the presence of a carbonyl compound $R^1$—CO—$R^2$, said process being described in German Offenlegungsschrift No. 2,155,544.

A number of the compounds falling within the scope of formula I have been disclosed in German Offenlegungsschrift No. 2,155,544 and in Yamamoto et al, J. Am. Chem. Soc. 103, 4186-4194 (1981). Other compounds are novel, however, and thus comprise part of the instant invention. These novel compounds correspond to the formula III

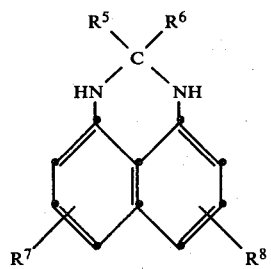
(III)

wherein (1) $R^5 = R^1$, $R^6 = R^2$ and $R^5R^6 = R^1R^2$ when $R^7$ is hydrogen or alkyl having 1 to 12 carbon atoms, $R^8$ is alkyl having 1 to 12 carbon atoms, or $R^7$ and $R^8$ together are 1,2-ethylene in the peri-position; or wherein (2) $R^5$ and $R^6$ are branched-chain alkyl having 6 to 18 carbon atoms or $R^5$ and $R^6$ together with the carbon atom to which they are attached form cycloalkane of 7 to 25 carbon atoms, alkylcycloalkane of 7 to 25 carbon atoms or cycloalkylcycloalkane of 9 to 25 carbon atoms, when $R^7$ and $R^8$ independently are hydrogen or alkyl having 1 to 12 carbon atoms or $R^3$ and $R^4$ together are 1,2-ethylene in the peri-position.

Compounds of interest within formula III include those wherein $R^5$ and $R^6$ are branched-chain alkyl having 6 to 18 carbon atoms or $R^5$ and $R^6$ together with the carbon atoms to which they are attached form alkylcycloalkane of 7 to 25 carbon atoms or cycloalkylcycloalkane of 10 to 25 carbon atoms and $R^7$ and $R^8$ independently are hydrogen or alkyl having 1 to 12 carbon atoms or $R^7$ and $R^8$ together are 1,2-ethylene in peri-position.

Other compounds of interest within formula III include those wherein $R^5$ and $R^6$ together with the carbon atom to which they are attached form a cycloalkane group having 5 to 20 carbon atoms, $R^7$ is hydrogen or alkyl having 1 to 12 carbon atoms and $R^8$ is alkyl having 1 to 12 carbon atoms or $R^7$ and $R^8$ together are 1,2-ethylene in peri-position.

These new compounds are, of course, prepared in the manner described hereinabove relative to the compounds of formula I.

The following examples will further illustrate the embodiments of the instant invention.

EXAMPLE 1

A mixture of 15.8 g (0.1 mole) of 1,8-diaminonaphthalene and 16.8 g (0.1 mole) of 4-t-amylcyclohexanone in 210 ml of toluene was heated under reflux. After the theoretical amount of water had been collected in a Dean-Stark trap (3 hours), about 70 ml of toluene was distilled off. The remaining solution was treated with 2.0 g of a filtration aid, filtered and the solvent removed in vacuo. Recrystallization from hexane gave 28.45 g (92% yield) of 2,3-dihydroperimidine-2-spiro(4-t-amylcyclohexane) as a tan solid, m.p. 113°–115° C. (Compound No. 1)

$C_{21}H_{28}N_2$ (308.50): Calc.: C 81.77, H 9.15, N 9.08%. Found: C 81.69, H 9.35, N 9.22%.

The following compounds were obtained in the same manner from 1,8-diaminonaphthalene and the corresponding carbonyl compounds:

2,3-dihydroperimidine-2-spiro(4-t-butyl-cyclohexane), from 4-t-butylcyclohexanone, light-brown solid, m.p. 168°–169° C. (Compound No. 2)

2,3-dihydroperimidine-2-spirocyclododecane, from cyclododecanone, gray solid, m.p. 195°-198° C. (Compound No. 3)

2,3-dihydroperimidine-2-spiro(decahydro-1-naphthalene), from 1-oxodecahydronaphthalene, gray solid, m.p. 161°-162° C. (Compound No. 4)

2,3-dihydroperimidine-2-spiro-8'tricyclo[5.2.1.0$^{2,6}$]decane, from 8-oxotricyclo[5.2.1.0$^{2,6}$]decane, pink glassy solid, m.p. 50°-60° C. (Compound No. 5)

2,2-dinonyl-2,3-dihydroperimidine, from dinonyl ketone, gray solid, m.p. 53°-54° C. (Compound No. 6)

2-methyl-2-(2-methyl-2-diethylphosphonopropyl)-2,3-dihyro perimidine, from 4-methyl-4-diethylphosphono-2-pentanone, pink solid, m.p. 102°-103° C. (Compound No. 7)

2-undecyl-2,3-dihydroperimidine, from dodecanal, pink solid m.p. 45°-50° C. (Compound No. 8)

2-(1-pentyl-1-octenyl)-2,3-dihydroperimidine, from 2-pentyl-2-nonenal, purified by column chromatography, pink oil (Compound No. 9)

$C_{24}H_{34}N_2$ (350.60): Calc.: C 82.23, H 9.78, N 7.99%. Formula: C 81.99, H 9.47, N 8.34%.

2-(3,5-di-t-butyl-4-hydroxyphenyl)-2,3-dihydroperimidine, from 3,5-di-t-butyl-4-hydroxybenzaldehyde, recrystallized from toluene, colorless solid, m.p. 227°-228° C. (Compound No. 10)

2,3-dihydroperimidine-2-spiro(2-cyclohexylcyclohexane), from 2-cyclohexyl-cyclohexanone, pink solid, crystallized from toluene as a 1:2 toluene inclusion complex, m.p. 208°-210° C. (Compound No. 11)

2,3-dihydroperimidine-2-spiro(4-cyclohexylcyclohexane), from 4-cyclohexyl-cyclohexane, tan solid, crystallized from toluene as a 1:2 toluene inclusion complex, m.p. 152°-154° C. (Compound No. 12)

2,3-dihydroaceperimidine-2-spiro(4-t-amylcyclohexane), from 5,6-diaminoacenaphthene and 4-t-amylcyclohexanone, tan solid, m.p. 122°-129° C. (Compound No. 13).

2,3-dihydroaceperimidine-2-spirocyclododecane, from 5,6-diaminoacenaphthene and cyclododecanone, tan solid, recrystallized from toluene, m.p. 202°-203° C. (Compound No. 14)

2,3-dihydroperimidine-2-spirocyclohexane, from cyclohexanone, colorless solid, crystallized from ethanol-water (2:1), m.p. 108°-110° C. (Compound No. 15).

2,3-dihydroperimidine-2-spiro(4-t-octylcyclohexane), from 4-t-octylcyclohexanone, pink glassy solid. (Compound No. 16).

EXAMPLE 2

15.8 g (0.1 mole) of 1,8-diaminonaphthalene and 16.0 g (0.1 mole) of 2,5,7-trimethyl-4-nonanone were dissolved in a mixture of 52 g of isobutanol, 24 g of water and 9 g of acetic acid and heated under reflux for 11 hours. After cooling, the solution was neutralized with 3.0 g of $K_2CO_3$. The organic layer was separated from the aqueous layer and filtered. The filtrate was evaporated in vacuo yielding a dark oily residue, which was thereafter dissolved in 2:1 hexane-diethylether and the solution filtered over alumina. After distilling off the solvent, 11.8 g of 2-isobutyl-2(2,4-dimethylpentyl)-2,3-dihydroperimidine was obtained as a semi-solid residue (Compound No. 17)

$C_{22}H_{32}N_2$ (324.50): Calc.: C 81.43, H 9.94, N 8.63%. Found: C 81.02, H 9.91, N 8.55%.

EXAMPLE 3

A solution of 3.2 g (0.02 mole) of 1,8-diaminonaphthalene and 3.0 g (0.02 mole) of p-dimethylaminobenzaldehyde in 35 ml of ethanol was refluxed for 2 hours. After cooling, the resulting precipitate was filtered and recrystallized from ethanol. There were obtained 3.8 g of 2-(p-dimethylaminophenyl)-2,3-dihydroperimidine as colorless crystals, m.p. 165°-166° C. (Compound No. 18).

$C_{19}H_9N_3$ (289.37): Calc.: C 78.86, H.6.62, N 14.52%. Found: C 78.96, H 6.64, N 14.45%.

EXAMPLE 4

The compounds of formula I were tested for their antioxidative effect in lubricants by the Rotary Bomb Oxidation Test (RBOT) according to ASTM D-2272.

In this test, 125 mg of the antioxidant and 5 ml of water are added to 50 g of a mineral oil (Exxon LO-5084). Thus, the concentration of the antioxidant amounts to 0.25%. The lubricant is placed in a glass container together with a copper coil. The glass container is placed in a steel bomb equipped with a pressure gage. The bomb is then charged with oxygen to a pressure of 90 psi (6.12 atm.), placed in an oil bath set at 150° C. and rotated axially at 100 rpm, at an angle of 30° from the horizontal. The test is completed after the pressure drops more than 25 psi (1.7 atm).

The time in minutes from the start of the test to the 25 psi pressure drop is reported in Table 1. As noted, the data show a significant improvement in stability toward oxidation when the instant perimidines are added to the oil.

TABLE 1

| Compound No. | Time (min.) | Compound No. | Time (min.) |
|---|---|---|---|
| 1 | 660 | 9 | 306 |
| 2 | 658 | 10 | 210 |
| 3 | 415 | 11 | 242 |
| 4 | 372 | 13 | 381 |
| 5 | 178 | 14 | 247 |
| 6 | 157 | 15 | 495 |
| 7 | 215 | 16 | 410 |
| 8 | 185 | 17 | 428 |
| | | 18 | 381 |
| Control (without antioxidant) | | | 30 |

EXAMPLE 5

Mixtures of compounds of formula I and commercial oil antioxidants were tested in the same manner as described in Example 4. As shown in Table 2, these mixtures exhibit a synergistic activity.

TABLE 2

| Additive | RBOT (min.) |
|---|---|
| 0.25% Compound No. 3 | 415 |
| 0.25% Irganox ® L 57 | 146 |
| 0.25 Irganox ® L 130 | 114 |
| 0.25% Irganox ® L 01 | 120 |
| 0.05% No. 3 + 0.20% Irganox ® L 57 | 315 |
| 0.05% No. 3 + 0.20% Irganox ® L 130 | 315 |
| 0.05% No. 3 + 0.10% Irganox ® L 57 + 0.10% Irganox ® L 130 | 434 |
| 0.05% No. 3 + 0.20% Irganox ® L 01 | 276 |
| 0.25% Compound No. 1 | 660 |
| 0.05% No. 1 + 0.20% Irganox ® L 57 | 382 |
| 0.05% No. 1 + 0.10% Irganox ® L 57 + 0.10% Irganox ® L 130 | 377 |
| 0.05% No. 1 + 0.20% Irganox ® L 01 | 303 |
| 0.25% Compound No. 11 | 306 |

TABLE 2-continued

| Additive | RBOT (min.) |
|---|---|
| 0.05% No. 11 + 0.20% Irganox ® L 130 | 232 |
| 0.05% No. 11 + 0.20% Irganox ® L 115 | 230 |
| 0.25 Compound No. 17 | 428 |
| 0.05% No. 17 + 0.20% Irganox ® L 01 | 229 |

Legend:
Irganox ® L57 = dialkyl diphenylamine
Irganox ® L130 = liquid phenolic antioxidant
Irganox ® L01 = 4,4'-dioctyldiphenylamine
Irganox ® L115 = thiodiethylene-bis(3,5-di-t-butyl-4-hydroxy-hydrocinnamate).
Irganox products from CIBA-GEIGY Corp.

In summary, this invention provides a novel class of lubricant antioxidants which exhibit excellent antioxidative performance. Variations may be made in procedures, proportions and materials without departing from the scope of the invention as defined in the following claims.

What is claimed is:

1. A lubricant composition comprising a mineral oil or a synthetic oil or mixtures thereof and an effective stabilizing amount of a compound of formula (I)

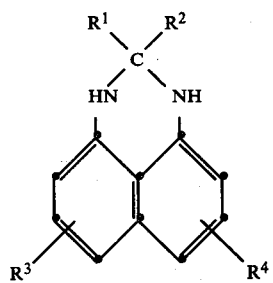

wherein $R^1$ is hydrogen or alkyl having 1 to 20 carbon atoms; $R^2$ is alkyl, phosphono-substituted alkyl, alkyl interrupted by O, alkyl interrupted by S, alkenyl having 3 to 16 carbon atoms, aryl, lower alkyl-substituted aryl, hydroxyl-substituted aryl, halogen-substituted aryl or di(lower) alkylamino-substituted aryl and wherein said alkyl group has from 1 to 20 carbon atoms and said aryl group has from 6 to 10 carbon atoms or $R^1$ and $R^2$ together with the carbon atom to which they are attached form cycloalkane of 5 to 25 carbon atoms, alkylcycloalkane of 6 to 25 carbon atoms or cycloalkylcycloalkane of 9 to 25 carbon atoms; and $R^3$ and $R^4$ independently are hydrogen or alkyl having 1 to 12 carbon atoms or $R^3$ and $R^4$ together are 1,2-ethylene in the peri-position.

2. A lubricant composition according to claim 1 containing a compound of formula I wherein $R^1$ is hydrogen or branched-chain alkyl having 4 to 18 carbon atoms and $R^2$ is branched-chain alkyl having 4 to 18 carbon atoms.

3. A lubricant composition according to claim 1 containing a compound of formula I wherein $R^1$ and $R^2$ together with the carbon atom to which they are attached form a cycloalkane, alkylcycloalkane or cycloalkylcycloalkane group having 10 to 20 carbon atoms.

4. A lubricant composition according to claim 1 containing a compound of formula I wherein $R^3$ and $R^4$ together form a 1,2-ethylene bridge in the peri-position.

5. A lubricant composition according to claim 1, wherein said compound is selected from the group consisting of 2,3-dihydroperimidine-2-spiro(4-t-amylcyclohexane), 2,3-dihydropermidine-2-spiro(4-t-butylcyclohexane), 2,3-dihydroperimidine-2-spirocyclododecane, 2,3-dihydroperimidine-2-spiro(decahydro-1-naphthalene), 2,3-dihydroperimidine-2-spiro-8'-tricyclo[5.2.1.0$^{2,6}$]decane, 2,2-dinonyl-2,3-dihydroperimidine, 2-methyl-2-(2-methyl-2-diethylphosphonopropyl)-2,3-dihydroperimidine, 2-undecyl-2,3-dihydroperimidine, 2-(1-pentyl-1-octenyl)-2,3-dihydroperimidine, 2-(3,5-di-t-butyl-4-hydroxyphenyl)-2,3-dihydroperimidine, 2,3-dihydroperimidine-2-spiro(2-cyclohexylcyclohexane), 2,3-dihydroperimidine-2-spiro(4-cyclohexylcyclohexane), 2,3-dihydroaceperimidine-2-spiro(4-t-amylcyclohexane), 2,3-dihydroaceperimidine-2-spirocyclododecane, 2,3-dihydroperimidine-2-spirocyclohexane, 2,3-dihydropermidine-2-spiro(4-t-octylcyclohexane), 2-isobutyl-2-(2,4-dimethylphenyl)-2,3-dihydroperimidine and 2-(p-dimethylaminophenyl)-2,3-dihydroperimidine.

* * * * *